United States Patent
King et al.

(10) Patent No.: US 7,205,051 B2
(45) Date of Patent: Apr. 17, 2007

(54) MEDICAL IMPLANT OR MEDICAL IMPLANT PART

(75) Inventors: Richard S. King, Warsaw, IN (US); Mark D. Hanes, Winona Lake, IN (US)

(73) Assignee: DePuy Products, Inc., Warsaw, IN (US)

( * ) Notice: Subject to any disclaimer, the term of this patent is extended or adjusted under 35 U.S.C. 154(b) by 268 days.

(21) Appl. No.: 10/675,047

(22) Filed: Sep. 30, 2003

(65) Prior Publication Data

US 2005/0069696 A1 Mar. 31, 2005

(51) Int. Cl.
  *B32B 27/32* (2006.01)
(52) U.S. Cl. .................. 428/516; 428/520; 428/522; 428/523
(58) Field of Classification Search .............. 427/2.24, 427/2.26; 428/516, 520, 522, 523
  See application file for complete search history.

(56) References Cited

U.S. PATENT DOCUMENTS

| 4,670,508 | A  | 6/1987  | Ohdaira et al. |
| 5,275,838 | A  | 1/1994  | Merrill |
| 6,818,172 | B2 | 11/2004 | King et al. |
| 2002/0125614 | A1 | 9/2002  | King et al. |
| 2003/0083433 | A1 | 5/2003  | James et al. |
| 2003/0125513 | A1 | 7/2003  | King |
| 2003/0144741 | A1 | 7/2003  | King et al. |
| 2003/0144742 | A1 | 7/2003  | King et al. |
| 2004/0210316 | A1 | 10/2004 | King et al. |
| 2004/0262809 | A1 | 12/2004 | Smith et al. |
| 2005/0065307 | A1 | 3/2005  | King et al. |
| 2006/0004168 | A1 | 1/2006  | Greer et al. |
| 2006/0149387 | A1 | 7/2006  | Smith et al. |
| 2006/0149388 | A1 | 7/2006  | Smith et al. |

FOREIGN PATENT DOCUMENTS

| DE | 227 328 A1 | 9/1985 |
| WO | WO 93/25247 A1 | 12/1993 |

OTHER PUBLICATIONS

Beauregard et al., *Biomedical Sciences Instrumentation* 35: 415-419 (Apr. 16, 1999).
Kurtz et al., *Biomaterials*: 20(18): 1659-1688 (1999).

*Primary Examiner*—D. S. Nakarani
(74) *Attorney, Agent, or Firm*—Leydig, Voit & Mayer, Ltd.

(57) ABSTRACT

The invention provides a medical implant or medical implant part comprising a body and a surface layer, wherein the surface layer comprises a mixture comprising at least one hydrophilic polymer and ultrahigh molecular weight polyethylene having a weight average molecular weight of about 400,000 atomic mass units or more. The invention also provides a method for producing such a medical implant or medical implant.

12 Claims, No Drawings

MEDICAL IMPLANT OR MEDICAL IMPLANT PART

FIELD OF THE INVENTION

This invention pertains to medical implants or medical implant parts comprised of ultrahigh molecular weight polyethylene and methods of producing and using the same.

BACKGROUND OF THE INVENTION

Ultrahigh molecular weight polyethylene ("UHMWPE") is commonly used in making orthopaedic implants, such as artificial hip joints. In recent years, it has become increasingly apparent that tissue necrosis and osteolysis at the interface of the orthopaedic implant and the host bone are primary contributors to the long-term loosening failure of prosthetic joints. It is generally accepted by orthopaedic surgeons and biomaterials scientists that this tissue necrosis and osteolysis is due, at least in part, to the presence of microscopic particles of UHMWPE produced during the wear of the UHMWPE components. The reaction of the body to these particles includes inflammation and deterioration of the tissues, particularly the bone to which the orthopaedic implant is anchored. Eventually, the orthopaedic implant becomes painful and/or loose and must be revised and/or replaced.

In order to increase the useful life of orthopaedic implants having UHMWPE parts, several attempts have been made to increase the wear resistance of the UHMWPE, thereby decreasing the number of wear particles that can cause tissue necrosis and/or osteolysis. One method for increasing the wear resistance of UHMWPE utilizes exposure to high-energy radiation, such as gamma radiation, in an inert or reduced-pressure atmosphere to induce cross-linking between the polyethylene molecules. This cross-linking creates a three-dimensional network of polyethylene molecules within the polymer which renders it more resistant to wear, such as adhesive wear. However, the free radicals formed upon irradiation of UHMWPE can also participate in oxidation reactions which reduce the molecular weight of the polymer via chain scission, leading to degradation of physical properties, embrittlement, and a significant increase in wear rate. Moreover, the three-dimensional network produced by the cross-linking reaction can reduce the mechanical properties of the UHMWPE.

There are several processes that have been developed to effectively and efficiently reduce the number of free radicals present in irradiated UHMWPE, all of which have met with varying degrees of success (see, e.g. U.S. Pat. No. 5,414, 049). Moreover, while the cross-linking of the UHMWPE and other known methods can increase the wear resistance of a medical implant or medial implant part comprising UHMWPE, such implants or implant parts can still produce microscopic wear particles of UHMWPE that can lead to the eventual failure of the medical implant or medical implant part.

A need exists for alternative orthopaedic implants comprising UHMWPE and methods for producing and using such implants. The invention provides such an implant and such methods. These and other advantages of the invention, as well as additional inventive features, will be apparent from the description of the invention provided herein.

BRIEF SUMMARY OF THE INVENTION

The invention provides a medical implant or medical implant part comprising a body and a surface layer, wherein the surface layer comprises a mixture comprising at least one hydrophilic polymer having a melt index of about 0.5 g/10 min or less and ultrahigh molecular weight polyethylene having a weight average molecular weight of about 400,000 atomic mass units or more.

The invention also provides a method for producing a medical implant or medical implant part comprising a body and a surface layer, the method comprising the steps of: (a) providing a compression mold for the medical implant or medical implant part having an internal volume, (b) providing a matrix of ultrahigh molecular weight polyethylene, wherein the ultrahigh molecular weight polyethylene has a weight average molecular weight of about 400,000 atomic mass units or more, (c) dispersing at least one hydrophilic polymer in the matrix of ultrahigh molecular weight polyethylene to produce a mixture comprising at least one hydrophilic polymer and ultrahigh molecular weight polyethylene, (d) filling at least a portion of the internal volume of the compression mold with the mixture obtained in step (c), (e) compressing the mixture contained within the compression mold for a time and under conditions sufficient to form a medical implant or medical implant part therefrom, and (f) removing the medical implant or medical implant part from the compression mold.

DETAILED DESCRIPTION OF THE INVENTION

The invention provides a medical implant or medical implant part comprising a body and a surface layer, wherein the surface layer comprises a mixture comprising at least one hydrophilic polymer and ultrahigh molecular weight polyethylene having a weight average molecular weight of about 400,000 atomic mass units or more.

The medical implant or medical implant part of the invention can be any suitable medical implant or medical implant part. Suitable medical implants or medical implant parts include, but are not limited to, the acetabular cup, the insert or liner of the acetabular cup, or trunnion bearings (e.g., between the modular head and the stem) of artificial hip joints, the tibial plateau, patellar button (patello-femoral articulation), and trunnion or other bearing components of artificial knee joints, the talar surface (tibiotalar articulation) and other bearing components of artificial ankle joints, the radio-numeral joint, ulno-humeral joint, and other bearing components of artificial elbow joints, the glenoro-humeral articulation and other bearing components of artificial shoulder joints, intervertebral disk replacements and facet joint replacements for the spine, temporo-mandibular joints (jaw), and finger joints.

As noted above, the medical implant or medical implant part comprises a body and a surface layer. The body of the medical implant or medical implant part can comprise any suitable material (e.g., any biocompatible material). The body of the medical implant or medical implant part desirably comprises, consists of, or consists essentially of a material having a mechanical strength sufficient to withstand the forces to which the medical implant or medical implant part will be subjected during its lifetime. In certain embodiments, the body of the medical implant or medical implant part comprises ultrahigh molecular weight polyethylene.

The surface layer of the medical implant or medical implant part comprises a mixture comprising at least one hydrophilic polymer and ultrahigh molecular weight polyethylene. The hydrophilic polymer and the ultrahigh molecular weight polyethylene preferably are substantially uniformly dispersed throughout the mixture. In view of the hydrophobic nature of ultrahigh molecular weight polyethylene, the hydrophilic polymer and the ultrahigh molecular weight polyethylene typically will be present in the mixture in two distinct phases. Preferably, the mixture resembles an emulsion in which globules of a discontinuous phase, which phase is comprised of the minor component of the matrix (e.g., hydrophilic polymer), are dispersed in a continuous phase, which phase is comprised of the major component of the matrix (e.g., ultrahigh molecular weight polyethylene).

The surface layer of the medical implant or medical implant part can be provided in any suitable size and/or shape. Generally, the surface layer of the medical implant or medical implant part has a thickness of about 1 mm or more (e.g., about 0.5 mm or more, about 0.75 mm or more, about 1.25 mm or more, about 1.5 mm or more, or about 2 mm or more). In certain embodiments, the surface layer of the medical implant or medical implant part has a thickness that extends through substantially all of the medical implant or medical implant part. The surface layer of the medical implant or medical implant part can have a thickness that extends through the entire medical implant or medical implant part, i.e., the body and surface layer are the same. The surface layer of the medical implant or medical implant part generally is coextensive with at least one surface of the medical implant or medical implant part. Preferably, the surface layer corresponds to an articulating surface of the medical implant or medical implant part.

The hydrophilic polymer can have any suitable melt index. Typically, the hydrophilic polymer has a melt index of about 5 g/10 min or less (e.g., about 4 g/10 min or less, about 3 g/10 min or less, about 2 g/10 min or less, or about 1 g/10 min or less). Preferably, the hydrophilic polymer has a melt index of about 0.5 g/10 min or less, more preferably about 0.45 g/10 min or less, even more preferably about 0.425 g/10 min or less, and most preferably about 0.4 g/10 min or less. The melt index of the hydrophilic polymer is determined in accordance with ASTM Standard D1238-88 (entitled, "Flow Rates of Thermoplastics by Extrusion Plastometer") using the following conditions: (i) 190° C., (ii), 21.6 kg weight, (iii) 20 cm$^3$ sample, and (iv) 5.5 minute preheat time. More specifically, the equipment used to determine the melt index of the hydrophilic polymer (i.e., the plastometer, the cylinder, the die, the piston, the heater, the thermometer, etc.) is the same as that defined in ASTM Standard D1238-88; however, the conditions under which the melt index is measured differ from those specified in the aforementioned standard. In particular, a 20 cm$^3$ sample of the hydrophilic polymer, which sample is provided as a homogeneous powder or pellets, is used to determine the melt index of the hydrophilic polymer. The 20 cm$^3$ sample is placed in the barrel of the plastometer while tamping the material to ensure that the entire sample is placed in the barrel and at least 90% of the volume of the barrel is filled with the sample. After the sample is loaded into the barrel of the plastometer, the piston is inserted into the barrel, and 10.8 kg of weight is placed on the piston. The timing of the 5.5 minute preheating cycle is then begun. During the preheat cycle, the weight on the piston is adjusted so that the sample extrudes from the barrel at a rate such that the lower two scribed marker lines on the piston reach the top of the barrel by the end of the 5.5 minute preheat cycle (+/−15 seconds). Immediately prior to the completion of the preheat cycle, the weight on the piston is increased to 21.6 kg. Once the lower of the two scribed marker lines on the piston reaches the top of the barrel, the extrudate is cut from the barrel, and a timed sampling cycle is begun. Typically, the sampling cycle is about 1 minute; however, the length of the sampling cycle can be shorter (e.g., 30 seconds) or longer (e.g., 2 minutes) depending on the rate at which the sample extrudes from the barrel of the plastometer. At the end of the sampling cycle, the extrudate is cut from the barrel and weighed. The melt index (in g/10 min) is then calculated using the weight of the extrudate and the duration of the sampling cycle.

The hydrophilic polymer can be any suitable hydrophilic polymer. Preferably, the hydrophilic polymer will not degrade at the compression molding temperatures typically used for ultrahigh molecular weight polyethylene and is capable of cross-linking with itself and another polymer (e.g., ultrahigh molecular weight polyethylene) using high-energy radiation (e.g., gamma radiation). The hydrophilic polymer preferably is a water-soluble, biocompatible polymer. As utilized herein, the term "biocompatible polymer" is used to refer to any polymer that is susceptible to implantation in a host (e.g., human host) and does not elicit any adverse reactions. Preferably, the hydrophilic polymer is a water-soluble, biocompatible polymer selected from the group consisting of poly(ethylene oxide), polyvinylpyrrolidone, poly(vinyl alcohol), mixtures thereof, and copolymers thereof.

The hydrophilic polymer can be present in the mixture comprising at least one hydrophilic polymer and ultrahigh molecular weight polyethylene in any suitable amount. Typically, the hydrophilic polymer comprises about 0.1 wt. % or more, preferably about 0.5 wt. % or more, or more preferably about 1 wt. % or more of the mixture based on the total weight of the mixture. The hydrophilic polymer typically comprises about 25 wt. % or less, preferably about 20 wt. % or less, or more preferably about 15 wt. % or less of the mixture based on the total weight of the mixture. Generally, the hydrophilic polymer comprises about 0.1 to about 25 wt. % of the mixture based on the total weight of the mixture.

The mixture of the surface layer also comprises ultrahigh molecular weight polyethylene. As utilized herein, the term "ultrahigh molecular weight polyethylene" refers to a polyethylene polymer having a weight average molecular weight of about 400,000 atomic mass units or more. Preferably, the ultrahigh molecular weight polyethylene has a weight average molecular weight of about 1,000,000 (e.g., about 2,000,000 or about 3,000,000) atomic mass units or more. Typically, the weight average molecular weight of the ultrahigh molecular weight polyethylene is less than 10,000,000 atomic mass units or less, more preferably about 6,000,000 atomic mass units or less. Ultrahigh molecular weight polyethylene suitable for use in the invention includes, but is not limited to, commercially available ultrahigh molecular weight polyethylene, such as GUR 1050 (weight average molecular weight of about 5,000,000 to about 6,000,000 atomic mass units) or GUR 1020 (weight average molecular weight of about 3,000,000 to about 4,000,000 atomic mass units) powdered ultrahigh molecular weight polyethylene from Ticona (Summit, N.J.). Preferably, the ultrahigh molecular weight polyethylene does not contain stabilizers, antioxidants, or other chemical additives which may have potential adverse effects in medical applications.

Preferably, at least a portion of the hydrophilic polymer is covalently bonded to at least a portion of the ultrahigh molecular weight polyethylene contained in the surface layer of the medical implant or medical implant part. The hydrophilic polymer and the ultrahigh molecular weight polyethylene can be covalently bonded to each other using any suitable means. For example, the hydrophilic polymer and the ultrahigh molecular weight polyethylene can be bonded to each other using a suitable chemical cross-linking agent. Preferably, the hydrophilic polymer and the ultrahigh molecular weight polyethylene are covalently bonded to each other by cross-linking using high-energy irradiation. The hydrophilic polymer and the ultrahigh molecular weight polyethylene can be irradiated by exposing the mixture comprising at least one hydrophilic polymer and ultrahigh molecular weight polyethylene and/or the medical implant or medical implant part to a suitable amount of gamma, x-ray, or electron beam radiation. Preferably, the mixture comprising at least one hydrophilic polymer and ultrahigh molecular weight polyethylene is irradiated by exposing the mixture to about 0.5 to about 10 Mrad (e.g., about 1.5 to about 6 Mrad) of gamma radiation using methods known in the art. While the mixture can be exposed to amounts of radiation falling outside of the aforementioned range, such amounts of radiation tend to produce a surface layer with unsatisfactory properties. In particular, radiation doses of less than about 0.5 Mrad generally provide insufficient cross-linking of the hydrophilic polymer and the ultrahigh molecular weight polyethylene. Furthermore, while doses of greater than 10 Mrad may be used, the additional cross-linking that is achieved generally is offset by the increased brittleness of the surface layer. When the hydrophilic polymer and the ultrahigh molecular weight polyethylene are bonded by exposing the mixture to high-energy radiation, the mixture preferably is irradiated in an inert or reduced-pressure atmosphere. The free radicals generated in the mixture (i.e., in the hydrophilic polymer and the ultrahigh molecular weight polyethylene) preferably are quenched following the irradiation of the mixture using any suitable method, many of which are known in the art.

The invention also provides a method for producing a medical implant or medical implant part comprising a body and a surface layer, the method comprising the steps of: (a) providing a compression mold for the medical implant or medical implant part having an internal volume, (b) providing a matrix of ultrahigh molecular weight polyethylene, wherein the ultrahigh molecular weight polyethylene has a weight average molecular weight of about 400,000 atomic mass units or more, (c) dispersing at least one hydrophilic polymer in the matrix of ultrahigh molecular weight polyethylene to produce a mixture comprising at least one hydrophilic polymer and ultrahigh molecular weight polyethylene, (d) filling at least a portion of the internal volume of the compression mold with the mixture obtained in step (c), (e) compressing the mixture contained within the compression mold for a time and under conditions sufficient to form a medical implant or medical implant part therefrom, and (f) removing the medical implant or medical implant part from the compression mold.

The characteristics of the medical implant or medical implant part produced by the method of the invention (e.g., the body, the surface layer, the hydrophilic polymer, the ultrahigh molecular weight polyethylene, etc.) can be the same as those set forth above for the medical implant or medical implant part of the invention.

As noted above, the method of the invention comprises providing a compression mold for the medical implant or medical implant part having an internal volume. The term "compression mold" is utilized herein to refer to a mold typically having two halves which, when joined together, define an internal volume (i.e., mold cavity). The compression mold can be provided in any suitable configuration. Generally, the compression mold is configured such that the internal volume of the compression mold (i.e., the mold cavity) defines the medical implant or medical implant part in a substantially complete form (i.e., in substantially the same form as will be used for implantation in the host). However, it will be understood that the medical implant or medical implant part produced by the method of the invention can also be subjected to further processing (e.g., machining) to provide the medical implant or medical implant in the final form used for implantation in the host.

The matrix of ultrahigh molecular weight polyethylene can be provided in any suitable form. Preferably, the matrix of ultrahigh molecular weight polyethylene comprises, consists essentially of, or consists of ultrahigh molecular weight polyethylene in a powdered or pelletized form.

At least one hydrophilic polymer is dispersed in the ultrahigh molecular weight polyethylene to produce a mixture (e.g., a substantially homogeneous mixture) comprising at least one hydrophilic polymer and ultrahigh molecular weight polyethylene. The hydrophilic polymer can be dispersed in the matrix of ultrahigh molecular weight polyethylene using any suitable means. Typically, the hydrophilic polymer and the ultrahigh molecular weight polyethylene are provided in a powdered or pelletized form, and the hydrophilic polymer is dispersed in the ultrahigh molecular weight polyethylene by dry blending the two components to form a mixture comprising the hydrophilic polymer and ultrahigh molecular weight polyethylene.

As noted above, at least a portion of the internal volume of the compression mold (i.e., mold cavity) is filled with the mixture comprising, consisting essentially of, or consisting of the hydrophilic polymer and ultrahigh molecular weight polyethylene. Preferably, the portion of the internal volume of the compression mold filled with the mixture comprises a portion of the surface layer of the medical implant or medical implant part. In such an embodiment, the surface layer preferably corresponds to an articulating surface of the medical implant or medical implant part. In another embodiment, substantially all of the internal volume of the compression mold preferably is filled with the mixture comprising at least one hydrophilic polymer and ultrahigh molecular weight polyethylene. When only a portion of the internal volume of the compression mold is filled with the mixture, the remaining portion of the internal volume of the compression mold (e.g., the portion of the compression mold corresponding to the body of the medical implant or medical implant part) is filled with another suitable material, preferably ultrahigh molecular weight polyethylene.

After at least a portion of the internal volume of the compression mold is filled, the mixture comprising at least one hydrophilic polymer and ultrahigh molecular weight polyethylene contained within the compression mold is compressed for a time and under conditions sufficient to form a medical implant or medical implant part therefrom. The mixture is compressed by any suitable means, such as by mating the two halves of the compression mold and applying an external force in a direction such that any substance contained within the mold (e.g., the mixture comprising at least one hydrophilic polymer and ultrahigh molecular weight polyethylene) is subjected to a compressive force. It will be further understood that the particular time and conditions (e.g., force applied to the compression mold) necessary to form a medical implant or medical implant part will depend upon several factors, such as the composition of the mixture (e.g., the type and/or amount of the hydrophilic polymer, and/or the molecular weight of the ultrahigh molecular weight polyethylene), the size (e.g., thickness) of the desired medical implant or medical implant part, as well as others.

In certain embodiments, the method of the invention further comprises the step of cross-linking at least a portion of the hydrophilic polymer and the ultrahigh molecular weight polyethylene. The hydrophilic polymer and the ultrahigh molecular weight polyethylene can be cross-linked using any suitable method (e.g., chemical cross-linking or high-energy irradiation). Preferably, the method of the invention further comprises (g) irradiating at least a portion of the mixture comprising at least one hydrophilic polymer and ultrahigh molecular weight polyethylene for a time and under conditions sufficient to cross-link at least a portion of the hydrophilic polymer and ultrahigh molecular weight polyethylene contained therein. The mixture comprising at least one hydrophilic polymer and ultrahigh molecular weight polyethylene can be irradiated at any suitable point, but preferably is irradiated after the completion of step (f). The time and conditions sufficient to cross-link at least a portion of the hydrophilic polymer and ultrahigh molecular weight can vary depending upon several factors. For example, the identity of the hydrophilic polymer, the thickness of the medical implant or medical implant part, the desired degree of cross-linking, and the desired depth of the cross-linking can impact the time and/or conditions required to cross-link the hydrophilic polymer and ultrahigh molecular weight polyethylene.

Preferably, the hydrophilic polymer and the ultrahigh molecular weight polyethylene are cross-linked by exposing the medical implant or medical implant part to high-energy radiation. The medical implant or medical implant part can be irradiated by exposure to a suitable amount of gamma, x-ray, or electron beam radiation. Preferably, the medical implant or medical implant part is exposed to about 0.5 to about 10 Mrad (e.g., about 1.5 to about 6 Mrad) of gamma radiation using methods known in the art. While the medical implant or medical implant part can be exposed to amounts of radiation falling outside of the aforementioned range, such amounts of radiation tend to produce a medical implant or medical implant part with unsatisfactory properties. In particular, radiation doses of less than about 0.5 Mrad generally provide insufficient cross-linking of the hydrophilic polymer and the ultrahigh molecular weight polyethylene. Furthermore, while doses of greater than 10 Mrad may be used, the additional cross-linking that is achieved generally is offset by the increased brittleness of the medical implant or medical implant part.

Preferably, the mixture comprising at least one hydrophilic polymer and ultrahigh molecular weigh polyethylene is irradiated in an inert or reduced-pressure atmosphere. Irradiating the mixture comprising at least one hydrophilic polymer and ultrahigh molecular weigh polyethylene (i.e., non-oxidizing) or reduced-pressure atmosphere reduces the effects of oxidation and chain scission reactions which can occur during irradiation in an oxidative atmosphere. Typically, the mixture comprising at least one hydrophilic polymer and ultrahigh molecular weigh polyethylene (e.g., the medical implant or medical implant part) is placed in an oxygen-impermeable package during the irradiation step. Suitable oxygen-impermeable packaging materials include, but are not limited to, aluminum, polyester coated metal foil (e.g., the Mylar® product available from DuPont Teijin Films), polyethylene terephthalate, and poly(ethylene vinyl alcohol). In order to further reduce the amount of oxidation which occurs during the irradiation of the mixture comprising at least one hydrophilic polymer and ultrahigh molecular weigh polyethylene, the oxygen-impermeable packaging may be evacuated (e.g., the pressure within the packaging may be reduced below the ambient atmospheric pressure) and/or flushed with an inert gas (e.g., nitrogen, argon, helium, or mixtures thereof) after the mixture comprising at least one hydrophilic polymer and ultrahigh molecular weight polyethylene (e.g., the medical implant or medical implant part) has been placed therein.

When at least a portion of the hydrophilic polymer and ultrahigh molecular weight polyethylene are cross-linked by irradiating the mixture comprising at least one hydrophilic polymer and ultrahigh molecular weight polyethylene, the method of the invention preferably further comprises (h) quenching a substantial portion of the free radicals generated in the mixture comprising at least one hydrophilic polymer and ultrahigh molecular weight polyethylene during the irradiation of the mixture in step (g). The free radicals contained within the irradiated portion of the mixture can be quenched using any suitable method. For example, the free radicals contained within the irradiated portion of the mixture comprising at least one hydrophilic polymer and ultrahigh molecular weight polyethylene can be quenched by heating the irradiated mixture to a temperature between room temperature and the melting point of ultrahigh molecular weight polyethylene in an oxygen-reduced, non-reactive atmosphere for a length of time sufficient to reduce the number of free radicals present in the mixture (see, e.g., U.S. Pat. Nos. 5,414,049, 6,174,934, and 6,228,900). Alternatively, the free radicals contained within the irradiated portion of the mixture comprising at least one hydrophilic polymer and ultrahigh molecular weight polyethylene can be quenched by heating the irradiated mixture to a temperature at or above the melting point of ultrahigh molecular weight polyethylene in an oxygen-reduced, non-reactive atmosphere for a length of time sufficient to reduce the number of free radicals present in the mixture (see, e.g., U.S. Pat. Nos. 6,017,975, 6,228,900, 6,242,507, and 6,316,158). Lastly, the free radicals contained within the irradiated portion of the mixture comprising at least one hydrophilic polymer and ultrahigh molecular weight polyethylene can be quenched by immersing the irradiated portion of the mixture in a non-polar solvent for a time and under conditions sufficient to quench a substantial portion of the free radicals contained therein. The aforementioned process is described more fully in copending U.S. patent application Ser. No. 10/609,749.

The method of the invention preferably further comprises the step of sterilizing the medical implant or medical implant part using a non-irradiative process. The medical implant or medical implant part can be sterilized at any suitable point, but preferably is sterilized after the completion of step (f), (g), or (h). Sterilizing the medical implant or medical implant part using a non-irradiative method avoids the formation of additional free radicals in the ultrahigh molecular weight polyethylene, which free radicals could undergo oxidative reactions resulting in the chain scission of the ultrahigh molecular weight polyethylene. Suitable non-irradiative sterilization techniques include, but are not limited to, gas plasma or ethylene oxide methods known in the art. For example, the packaged medical implant or packaged medical implant part can be sterilized using a PlazLyte® Sterilization System (Abtox, Inc., Mundelein, Ill.) or in accordance with the gas plasma sterilization processes described in U.S. Pat. Nos. 5,413,760 and 5,603,895.

The medical implant or medical implant part can be packaged in any suitable packaging material. Desirably, the packaging material maintains the sterility of the medical implant or medical implant part until the packaging material is breached. If the medical implant or medical implant part has not been irradiated or if the medical implant or medical implant part has been irradiated and a substantial portion of the free radicals contained within the medical implant or medical implant part have been quenched, the medical implant or medical implant part will be relatively stable to atmospheric oxidation. Under such circumstances, it would not be necessary to package the medical implant or medical implant part in an inert atmosphere and, therefore, the medical implant or medical implant part could be packaged in an air-impermeable or air-permeable packaging material.

The following examples further illustrate the invention but, of course, should not be construed as in any way limiting its scope.

EXAMPLE 1

This example demonstrates the properties of a medical implant or medical implant part of the invention. This example further demonstrates the production of a medical implant or medical implant part according to the method of the invention. Approximately 2 g of powdered poly(ethylene oxide) (WSR-303 available from Dow, Midland, Mich.), which has a weight average molecular weight of approximately 7.0 million atomic mass units and a melt index of less than about 0.5 g/10 min, was dry blended with approximately 23 g of powdered ultrahigh molecular weight polyethylene (GUR 1020 available from Ticona, Summit, N.J.). The mixture comprised approximately 8 wt. % of poly(ethylene oxide), which is equivalent to approximately 6.4% by volume. The mixture of poly(ethylene oxide) and ultrahigh molecular weight polyethylene was then placed in a compression mold and compressed under a suitable temperature and pressure until the ultrahigh molecular weight polyethylene consolidated to produce a composite of the poly(ethylene oxide) and ultrahigh molecular weight polyethylene.

The average contact angle of a drop of water on the surface of the composite of poly(ethylene oxide) and ultrahigh molecular weight polyethylene was then measured and compared to the contact angle of a drop of water on the surface of virgin ultrahigh molecular weight polyethylene. The contact angle for each sample was determined by dispensing a water drop on the surface of the samples and then measuring, after about 3 to 5 minutes, the angle between the surface of the sample and the surface of the water drop at the point of contact between the two. The average contact angle for the composite of poly(ethylene oxide) and ultrahigh molecular weight polyethylene was approximately 85 degrees. The average contact angle for the virgin ultrahigh molecular weight polyethylene was approximately 90 degrees.

These results demonstrate that the attraction between water and the surface of a composite comprising a mixture of a hydrophilic polymer and ultrahigh molecular weight polyethylene is relatively greater than the attraction between water and the surface of virgin ultrahigh molecular weight polyethylene. More specifically, the reduced contact angle of the composite of poly(ethylene oxide) and ultrahigh molecular weight polyethylene relative to the virgin ultrahigh molecular weight polyethylene evinces the relatively greater attraction between water and the surface of the composite of poly(ethylene oxide) and ultrahigh molecular weight polyethylene relative to the surface of virgin ultrahigh molecular weight polyethylene.

EXAMPLE 2

This example demonstrates the properties of a medical implant or medical implant part of the invention. This example also demonstrates the production of a medical implant or medical implant part according to the method of the invention. Approximately 2 g of powdered poly(ethylene oxide) (WSR-303 available from Dow, Midland, Mich.), which has a weight average molecular weight of approximately 7.0 million atomic mass units and a melt index of less than 0.5 g/10 min, was dry blended with approximately 23 g of powdered ultrahigh molecular weight polyethylene (GUR 1020 available from Ticona, Summit, N.J.). The mixture comprised approximately 8 wt. % of poly(ethylene oxide), which is equivalent to approximately 6.4% by volume. The mixture of poly(ethylene oxide) and ultrahigh molecular weight polyethylene was then placed in a compression mold and compressed under a suitable temperature and pressure until the ultrahigh molecular weight polyethylene consolidated to produce a composite of the poly(ethylene oxide) and ultrahigh molecular weight polyethylene.

The composite of poly(ethylene oxide) and ultrahigh molecular weight polyethylene was then packaged in aluminum foil, and the air was evacuated from the foil packaging. The packaged composite was irradiated by exposing the composite to approximately 50 kGy (approximately 5 Mrad) of gamma radiation and then heated to 140° C. in a vacuum oven for about 2 hours to quench a substantial portion of the free radicals produced in the composite during the irradiation process.

The average contact angle of a drop of water on the surface of the irradiated composite of poly(ethylene oxide) and ultrahigh molecular weight polyethylene was then measured and compared to the contact angle of a drop of water on the surface of virgin ultrahigh molecular weight polyethylene. The contact angle for each sample was determined by dispensing a water drop on the surface of the samples and then measuring, after about 3 to 5 minutes, the angle between the surface of the sample and the surface of the water drop at the point of contact between the two. The average contact angle for the irradiated composite of poly(ethylene oxide) and ultrahigh molecular weight polyethylene was approximately 73 degrees. However, the average contact angle for the irradiated composite decreased to approximately 54 degrees after the irradiated composite was soaked in water for about one hour before the contact angle measurements were taken. The average contact angle for the virgin ultrahigh molecular weight polyethylene was approximately 90 degrees.

These results demonstrate that an irradiated composite comprising a mixture of a hydrophilic polymer and ultrahigh molecular weight polyethylene exhibits improved hydrophilicity relative to virgin ultrahigh molecular weight polyethylene. More specifically, the reduced contact angle of the irradiated composite of poly(ethylene oxide) and ultrahigh molecular weight polyethylene relative to the virgin ultrahigh molecular weight polyethylene evinces the improved hydrophilicity of the irradiated composite of poly(ethylene oxide) and ultrahigh molecular weight polyethylene relative to the virgin ultrahigh molecular weight polyethylene. Furthermore, the contact angle measurements taken after soaking the irradiated composite in water demonstrates that the hydrophilicity of the irradiated composite improves as the irradiated composite absorbs water from an aqueous environment (e.g., the human body).

EXAMPLE 3

This example demonstrates the optional cross-linking of the hydrophilic polymer and ultrahigh molecular weight polyethylene in a medical implant or medical implant part according to the invention. Three composites (Composite 3A, 3B, and 3C) comprising a mixture of a hydrophilic polymer (i.e., poly(ethylene oxide)) and ultrahigh molecular weight polyethylene were prepared in accordance with the procedures set forth in Example 1 (Composite 3A) and Example 2 (Composite 3C). Composite 3B was generally prepared in accordance with the procedure set forth in Example 2, but the composite was not subjected to the quench process following gamma irradiation. Each composite was then submerged in a sonicated water bath for approximately 24 hours at a temperature of approximately 65° C. The composites then were removed from the water bath, dried, and weighed to determine the change in weight due to submersion in the water bath. The results of the measurements are summarized below in Table 1.

TABLE 1

Irradiation Doses, Quench Particulars, and Weight Loss for Composites 3A–3C.

| Composite | Radiation Dose | Quench | Weight Loss (wt. % based on initial weight of poly(ethylene) oxide) |
|---|---|---|---|
| 3A | — | — | 17 |
| 3B | 50 kGy (5 Mrad) | — | 5.6 |
| 3C | 50 kGy (5 Mrad) | 2 hours at 140° C. | No detectable weight loss |

As evidenced by the data set forth in Table 1, the hydrophilic polymer and the ultrahigh molecular weight polyethylene of the composite can be cross-linked by irradiating the composite. In particular, the different weight loss for each composite suggests that the hydrophilic polymer and ultrahigh molecular weight polyethylene in each composite are associated in different ways and/or to different degrees. For example, Composite 3A, which was not irradiated, lost approximately 17 wt. % of the initial poly(ethylene oxide) present in the composite after submersion in the water bath. By way of contrast, Composites 3B and 3C, which were both irradiated, lost only approximately 5.6 wt. % and no detectable amount, respectively, of the initial poly(ethylene oxide) present in the composite after submersion in the water bath. Insofar as the poly(ethylene oxide) is the only water-soluble component present in the composites, the observed weight loss for Composites 3A and 3B must be solely attributable to the dissolution of the poly(ethylene oxide) at the surface of the composites. Furthermore, the free radicals produced in the ultrahigh molecular weight polyethylene and hydrophilic polymer during the irradiation process would, at least in part, interact with each other and combine to produce cross-links between the two polymers. Thus, this data indirectly demonstrates that the hydrophilic polymer (i.e., poly(ethylene oxide)) has cross-linked with the ultrahigh molecular weight polyethylene, thereby preventing the hydrophilic polymer from dissolving in the water bath.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A medical implant or medical implant part comprising a body and a surface layer, wherein the surface layer is formed from a mixture comprising at least one hydrophilic polymer having a melt index of about 0.5 g/10 min or less and an ultrahigh molecular weight polyethylene having a weight average molecular weight of about 400,000 atomic mass units or more, wherein the hydrophilic polymer is poly(ethylene oxide) or a copolymer thereof.

2. The medical implant or medical implant part of claim 1, wherein the ultrahigh molecular weight polyethylene has a weight average molecular weight of about 1,000,000 atomic mass units or more.

3. The medical implant or medical implant part of claim 1, wherein at least a portion of the hydrophilic polymer is covalently bonded to at least a portion of the ultrahigh molecular weight polyethylene.

4. The medical implant or medical implant part of claim 1, wherein the hydrophilic polymer is a water-soluble, biocompatible polymer.

5. The medical implant or medical implant part of claim 4, wherein the hydrophilic polymer comprises about 0.1 to about 25 wt. % of the mixture comprising at least one hydrophilic polymer and ultrahigh molecular weight polyethylene.

6. The medical implant or medical implant part of claim 1, wherein the hydrophilic polymer is a water-soluble, biocompatible poly(ethylene oxide).

7. The medical implant or medical implant part of claim 1, wherein the surface layer has a thickness of about 1 mm or more.

8. The medical implant or medical implant part of claim 1, wherein the body comprises ultrahigh molecular weight polyethylene.

9. The medical implant or medical implant part of claim 1, wherein the body is composed of the same materials as the surface layer.

10. The medical implant or medical implant part of claim 1, wherein the surface layer corresponds to an articulating surface of the medical implant or medical implant part.

11. A medical implant or medical implant part comprising a body and a surface layer, wherein the surface layer comprises at least one hydrophilic polymer having a melt index of about 0.5 g/10 min or less and ultrahigh molecular weight polyethylene having a weight average molecular weight of about 400,000 atomic mass units or more, wherein the hydrophilic polymer and the ultrahigh molecular weight polyethylene have been crosslinked, wherein the hydrophilic polymer is poly(ethylene oxide) or a copolymer thereof.

12. The medical implant or medical implant part of claim 11, wherein at least a portion of the hydrophilic polymer is covalently bonded to at least a portion of the ultrahigh molecular weight polyethylene.

* * * * *